United States Patent [19]

Rodriguez et al.

[11] 4,271,173

[45] Jun. 2, 1981

[54] 6-AMINO-SPIRO[PENAM-2,4'-PIPERIDINE]-3-CARBOXYLIC ACID, ANTIBACTERIAL COMPOSITIONS THEREOF AND METHOD OF USE THEREOF

[75] Inventors: Ludovic Rodriguez, Brussels; Jacques Leclercq, Braine l'Alleud; Pierre Ykman; Eric Cossement, both of Brussels, all of Belgium

[73] Assignee: U C B, Societe Anonyme, Saint-Gilles-lez-Brussels, Belgium

[21] Appl. No.: 162,615

[22] Filed: Jun. 24, 1980

[30] Foreign Application Priority Data

Jun. 25, 1979 [GB] United Kingdom ............... 22055/79

[51] Int. Cl.³ ................ C07D 499/32; A61K 31/425; A61K 31/43
[52] U.S. Cl. ...................................... 424/267; 546/17; 260/239.3 R; 548/147; 260/245.2 R; 260/239.1
[58] Field of Search .......................... 546/17; 548/147; 260/239.3 R, 239.1, 245.2; 424/267

[56] References Cited

U.S. PATENT DOCUMENTS

| | | | |
|---|---|---|---|
| 4,091,027 | 5/1978 | Rodriguez et al. | 548/147 |
| 4,137,236 | 1/1979 | Rodriguez et al. | 548/147 |
| 4,139,628 | 2/1979 | Rodriguez et al. | 548/147 |
| 4,145,343 | 3/1979 | Rodriguez et al. | 548/147 |

*Primary Examiner*—Robert T. Bond
*Attorney, Agent, or Firm*—Wenderoth, Lind & Ponack

[57] ABSTRACT

6-Amino-spiro[penam-2,4'-piperidine]-3-carboxylic acid derivatives having the formula

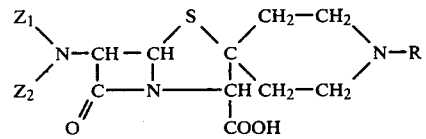

wherein R is a methyl, phenyl or benzyl radical, $Z_1$ is a hydrogen atom and $Z_2$ is a radical selected from those known from penicillin chemistry and is preferably a 2-phenylacetyl, 2-amino-2-phenylacetyl, 5-methyl-3-phenyl-4-isoxazolecarbonyl or 2,6-dimethoxybenzoyl radical, or $Z_1$ and $Z_2$ together represent a bivalent radical $Z_3$ and preferably a (hexahydro-1H-azepin-1-yl)methylene radical, as well as the pharmaceutically acceptable non-toxic salts thereof and process for preparing the same.

These compounds have valuable antibacterial properties and are useful as therapeutic agents in the treatment of infectious diseases caused by Gram-positive and Gram-negative bacteria.

10 Claims, No Drawings

6-AMINO-SPIRO[PENAM-2,4'-PIPERIDINE]-3-CARBOXYLIC ACID, ANTIBACTERIAL COMPOSITIONS THEREOF AND METHOD OF USE THEREOF

The present invention relates to new antibacterially active 6-amino-spiro[penam-2,4'-piperidine]-3-carboxylic acid derivatives and to the preparation and use thereof.

The new derivatives of 6-amino-spiro[penam-2,4'-piperidine]-3-carboxylic acid according to the present invention are compounds of the general formula:

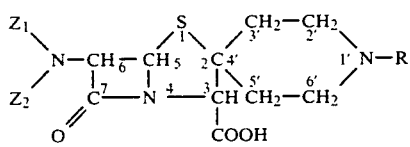

wherein R is a methyl, phenyl or benzyl radical, $Z_1$ is a hydrogen atom and $Z_2$ is a radical selected from those known from the chemistry of the penicillins and is preferably a 2-phenylacetyl, 2-amino-2-phenylacetyl, 5-methyl-3-phenyl-4-isoxazolecarbonyl or 2,6-dimethoxybenzoyl radical or $Z_1$ and $Z_2$ together represent a bivalent radical $Z_3$ and preferably a (hexahydro-1H-azepin-1-yl) methylene radical; as well as the pharmaceutically acceptable non-toxic salts thereof.

It is known that, generally speaking, the penicillins are a group of compounds having the general formula:

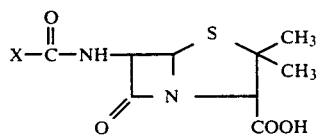

in which X represents a wide variety of substituents, the most commonly used of which are mentioned in Ullmanns Encyklopädie der Technischen Chemie, 4th Edition, vol. 7, (1974), 651–652.

Most of the investigations carried out to date were based on the search for new X substituents, while the basic ring system of the molecule remained unchanged. Nevertheless, some attempts have been made to study the effect of certain variations in the ring system on the activity of the resulting compounds. For example, new compounds have been suggested which are similar to the penicillins but in which the gem-dimethyl group in the 2-position was replaced by other groups. Subsequently, the following groups were proposed:

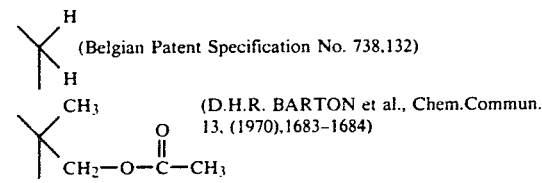

However, at the time of these various attemps, it was concluded that the nature of the substituents on the carbon atom in the 2-position was not essential to the antibacterial activity of the penicillins or like compounds (see, for example, in this respect R. J. STOODLEY, Progress in Organic Chemistry, 8, (1973), 106). Still more recently, the following groups have been proposed:

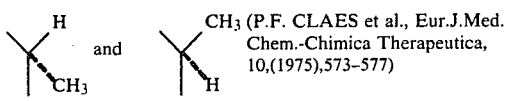

The conclusion as to antibacterial activity was the same.

We have now found that by appropriately substituting the carbon atom in the 2-position, it is possible to obtain compounds which not only have antibacterial activities superior to those of the corresponding penicillins but which are also particularly interesting in the treatment of infections caused by bacteria which are resistant to penicillins due to the production of beta-lactamases, i.e. enzymes which suppress the activity of the antibiotic by hydrolysis of its lactam ring: these new compounds and the preparation and use thereof constitute the subject matter of the present invention.

In the present Specification, the nomenclature used is that proposed by R. J. STOODLEY, loc. cit., pp. 102–103. In particular, the term "penam" is used for the following ring system:

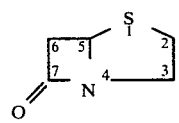

The new compounds of the present invention are 6-amino-spiro[penam-2,4'-piperidine]-3-carboxylic acids in which the amino group in the 6-position is substituted by a substituent which is known from penicillin chemistry. They are compounds which are similar to the penicillins but in which the carbon atom in the 2-position of the penam ring is substituted by a bivalent 3-azaspentamethylene chain which forms with this carbon atom a heterocycle.

Therefore, these new compounds comprise a spiro heterocycle constituted by the penam ring and by a saturated monocyclic heterocycle which has one nitrogen atom i.e. a piperidine ring.

Among the substituents known from penicillin chemistry, referred to hereinabove, particular mention is made of those referred to in Ulmmans Encyklopädie der Technischen Chemie, loc.cit.

By way of example, when $Z_1$ is a hydrogen atom and $Z_2$ is a 2-phenylacetyl radical, the compounds of the present invention are similar to benzylpenicillin (penicillin G); when $Z_1$ is a hydrogen atom and $Z_2$ is a 2-amino-2-phenylacetyl radical, the compounds of the present invention are similar to ampicillin; when $Z_1$ is a hydrogen atom and $Z_2$ is a 5-methyl-3-phenyl-4-isoxazolecarbonyl radical, the compounds of the present invention are similar to oxacillin and when $Z_1$ is a hydrogen atom and $Z_2$ is a 2,6-dimethoxybenzoyl radical, the compounds of the present invention are similar to methicillin. When $Z_1$ and $Z_2$ together represent a (hexahydro-1H-azepin-1-yl)methylene radical, the compounds of the present invention are similar to the penicillins described in British patent specification No. 1,293,590. In this case, the compounds have side chains bonded to the penam ring system by an

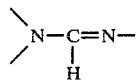

group and these compounds are called amidino-penicillins. This type of side chain was introduced recently into penicillin chemistry and it results in compounds, the activity of which at the level of the bacterial cell wall results from a mechanism which is different from that of the penicillins having traditional side chains, such as those defined hereinabove. The difference in their mode of action on the bacteria imparts to the amidino-penicillins a novel antibacterial spectrum.

With regard to stereochemistry, the existence of three asymmetric carbon atoms at $C_3$, $C_5$ and $C_6$ should lead to the formation of 8 isomers which can be grouped together into 4 racemic diastereoisomers. The kinetics of the reactions leads, in fact, to the formation solely of the three alpha, beta- and gamma-recemates. Preferably, the alpha-racemate is isolated from the reaction mixture, one of the optical antipodes of which has a configuration corresponding to that of penicillin. The alpha-racemate thus isolated is a mixture of isomers (dl) of configurations (3S, 5R, 6R)+(3R, 5S, 6S).

The compounds of general formula (I) according to the present invention, in which $Z_1$ is a hydrogen atom and $Z_2$ is a radical known from penicillin chemistry and preferably selected from the 2-phenylacetyl, 2-amino-2-phenylacetyl, 5-methyl-3-phenyl-4-isoxazolecarbonyl and 2,6-dimethoxybenzoyl radicals, are obtained by reacting an ester and preferably a benzyl ester of a 6-amino-spiro[penam-2,4'-piperidine]-3-carboxylic acid of the formula:

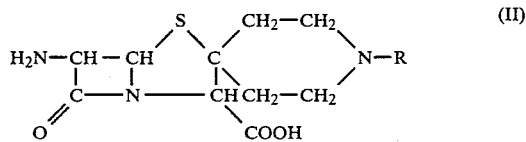

in which R has the same meaning as above, with a compound of the formula $Z_2Y$ (III) in which $Z_2$ has the meaning given above and Y is a halogen atom or a hydroxyl group, and converting the resulting ester into the corresponding acid by hydrogenolysis.

The compounds of formula (II) used as starting materials for the preparation of compounds of general formula (I) are preferably used in the form of their salts with p-toluenesulfonic acid.

The compounds of formula (III) used for acylating the amino group in the 6-position can be acid halides (Y=halogen) or free acids (Y=OH); in the latter case, acylation is carried out in the presence of a coupling agent, for example a carbodiimide, such as diisopropylcarbodiimide. Furthermore, when the compounds of formula (III) contain an amino group, this can be protected in known manner, for example by a benzyloxycarbonyl radical, which is subsequently eliminated during the hydrogenolysis step.

The 6-amino-spiro[penam-2,4'-piperidine]-3-carboxylic acids of formula (II) and, in particular, their benzyl esters which are used as starting materials, as well as the method of preparing them, are the subject matter of our Application Ser. No. 06/162,616, filed June 24, 1980, to which reference is made for a more detailed description.

The compounds of formula (II) can be prepared in the following way:

(1) reacting tert-butyl 2-formyl-2-phthalimido-acetate of formula (IV) with an alpha-amino-4-mercapto-1-R-4-piperidineacetic acid of formula (V) to give the gamma-isomer of a tert-butyl 4-carboxy-alpha-phthalimido-8-R-1-thia-3,8-diazaspiro[4.5] decane-2-acetate of formula (VI), according to the equation:

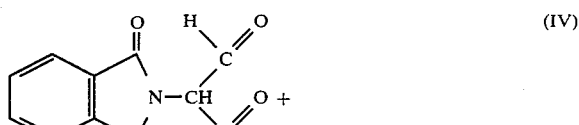

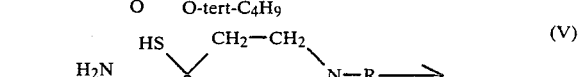

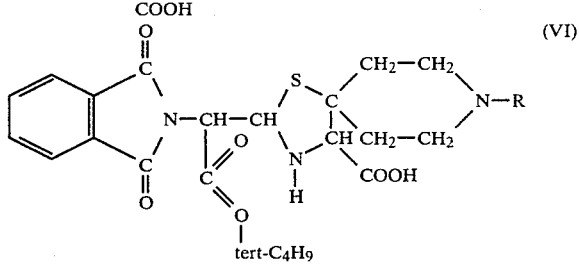

(2) epimerizing the gamma-isomer of formula (VI) to the alpha-isomer of formula (VII) by heating with pyridine or with diethylamine, according to the equation:

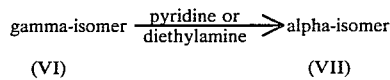

(3) preparing the tert-butyl 4-benzyloxycarbonyl-alpha-phthalimido-8-R-1-thia-3,8-diazaspiro[4.5]decane-2-acetate of formula (VIII) by reacting the alpha-isomer of formula (VII) with diazophenylmethane or with a benzyl halide according to the equation:

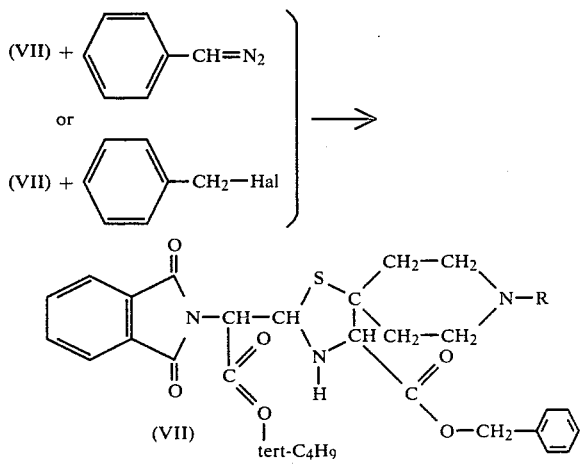

(4) subjecting the compound of formula (VIII) to dephthalimidation by hydrazinolysis, to give a tert-butyl alpha-amino-4-benzyloxycarbonyl-8-R-1-thia-3,8-diazaspiro[4.5]decane-2-acetate of formula (IX), according to the equation:

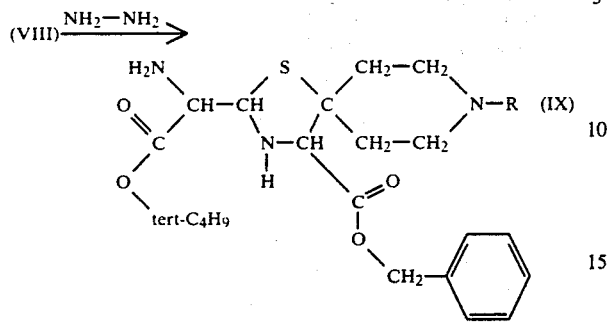

(5) selectively dealkylating the tert-butyl ester group of compound (IX) by treating it in solution in nitromethane with gaseous hydrogen chloride, to give alpha-amino-4-benzyloxycarbonyl-8-R-1-thia-3,8-diazaspiro[4.5]decane-2-acetic acid dihydrochloride of formula (X), according to the equation:

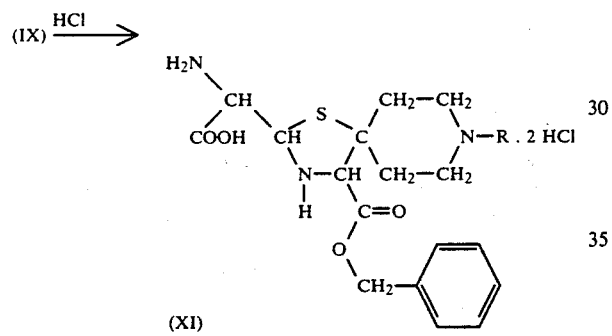

(6) blocking the alpha-amino group of compound (X) by means of trityl chloride to give 4-benzyloxycarbonyl-8-R-alpha-tritylamino-1-thia-3,8-diazaspiro[4.5]decane-2-acetic acid of formula (XI), according to the equation:

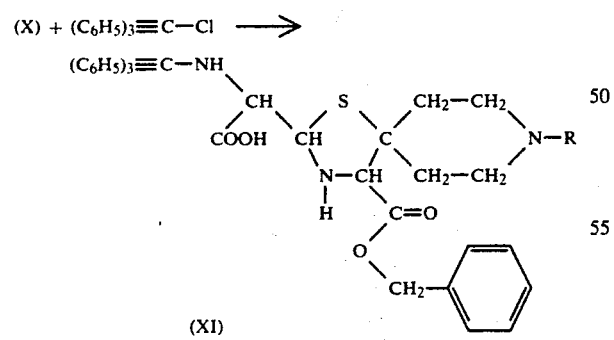

(7) cyclizing the compound of formula (XI), preferably at an elevated temperature, by reacting with a carbodiimide (abbreviated to CI), to give a benzyl 1'-R-6-tritylamino-spiro[penam-2,4'-piperidine]-3-carboxylate of formula (XII), according to the equation:

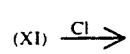

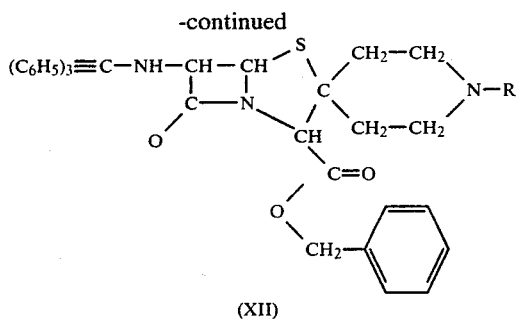

(8) and finally treating the compound of formula (XII) with p-toluenesulfonic acid (p-TS) to give a benzyl 6-amino-1'-R-sprio[penam-2,4'-piperidine]-3-carboxylate of formula (II), in the form of a di-p-toluenesulfonate, according to the equation:

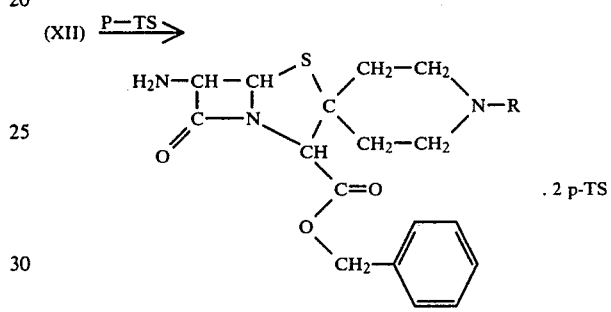

In the above formulae, R is a methyl, phenyl or benzyl radical.

The preparation of tert-butyl 2-formyl-2-phthalimido-acetate of formula (IV) is described in the literature (J. SHEEHAN et al., J. Am. Chem. Soc. 76, (1954), 158-160).

The preparation of an alpha-amino-4-mercapto-1-R-4-piperidineacetic acid of formula (V) can be effected in the following manner:

(a) reacting ethyl 2-isocyanoacetate with a 1-R-4-piperidone in the presence of a suspension of sodium hydride in tetrahydrofuran to give ethyl alpha-formamido-1-R-piperidine-$\Delta^{4,alpha}$-acetate, according to the equation:

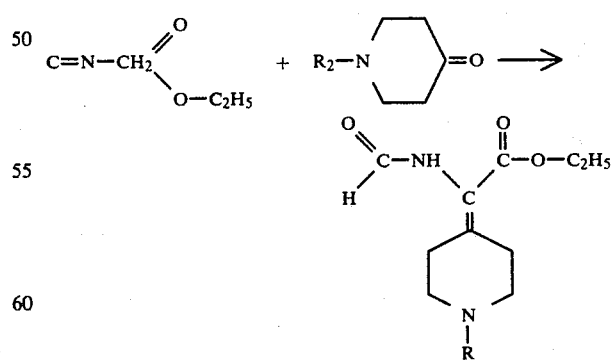

(b) heating ethyl alpha-formamido-1-R-piperidine-$\Delta^{4,alpha}$-acetate under reflux with phosphorus pentasulfide in solution in acetonitrile to give ethyl 8-R-1-thia-3,8-diazaspiro[4.5]dec-2-ene-4-carboxylate, according to the equation:

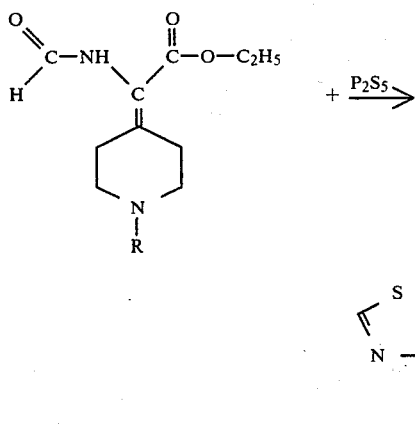

(c) decyclizing ethyl 8-R-1-thia-3,8-diazaspiro[4.5]-dec-2-ene-4-carboxylate by heating with aqueous hydrochloric acid to give the desired alpha-amino-4-mercapto-1-R-4-piperidineacetic acid of formula (V) in the form of a dihydrochloride, according to the equation:

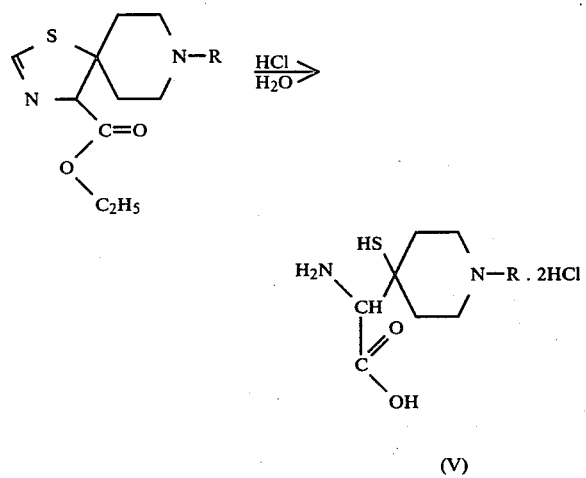

(V)

In the above formulae, R is a methyl, phenyl or benzyl radical.

If necessary, it is possible to separate the two enantiomeric forms of the compounds of formula (V), which makes it possible directly to obtain the optically pure diastereoisomer (VI).

Within the scope of the present invention, the term "pharmaceutically acceptable non-toxic salts" is to be understood to mean, in particular, metal salts, such as sodium, potassium, calcium and aluminum salts, ammonium salts and salts of amines, such as trialkylamines, particularly triethylamine, procaine, dibenzylamine, N-benzyl-beta-phenethylamine, L-ephenamine, N,N'-dibenzylethylenediamine, dehydroabietylamine, N,N'-bis-dehydroabietyl-ethylenediamine and the N-(lower alkyl)piperidines, such as N-ethylpiperidine, and, more generally, the salts already known for penicillins G and V (see Ullmanns Encyklopädie loc. cit., p. 653). These salts may be obtained from the corresponding acids by known methods.

In the particular case in which $Z_2$ is the 2-amino-2-phenylacetyl radical, the compounds of the present invention can be converted into their acid addition salts, for example with pharmaceutically acceptable non-toxic acids, such as acetic, citric, succinic, ascorbic, hydrochloric, hydrobromic, sulfuric and phosphoric acids.

The compounds of general formula (I), in which $Z_1$ and $Z_2$ together represent a bivalent radical $Z_3$ and preferably a (hexahydro-1H-azepin-1-yl)methylene radical, can be prepared by reacting a 6-amino-spiro[penam-2,4'-piperidine]-3-carboxylic acid of formula (II) or an ester thereof with an activated derivative of a compound of the formula $Z_3=O$ and preferably with an activated derivative of hexanhydro-1H-azepine-1-carboxaldehyde.

The activated derivative of the compound $Z_3=O$ is, for example and preferably the corresponding amide chloride obtained by reaction with oxalyl chloride, or a complex obtained by reaction with dimethyl sulfate. Preferably, the compounds of the following formulae are used, these being activated derivatives of hexahydro-1H-azepine-1-carboxaldehyde:

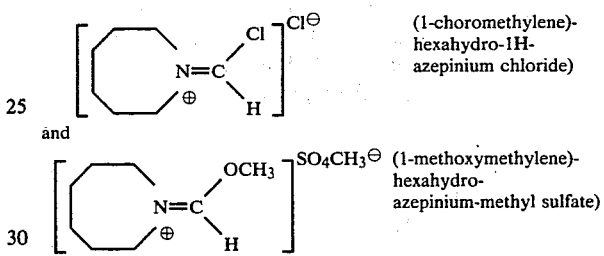

The present invention also relates to the use of compounds of general formula (I) and of their pharmaceutically acceptable non-toxic salts as antibacterial agents, as dietetic supplements in animal feeds and as therapeutic agents for man and animals in the treatment of infections diseases caused by Gram-positive or Gram-negative bacteria.

The compounds according to the present invention have a very broad spectrum of antibacterial activity, both against Gram-positive and Gram-negative bacteria but they are particularly effective for combating resistant strains of bacteria which produce beta-lactamases.

The following Examples are given for the purpose of illustrating the present invention:

EXAMPLE I

Preparation of 6-(2-phenylacetamido)-spiro[penam-2,4'-piperidine]-3-carboxylic acids

I.1. Preparation of 1'-methyl-6-(2-phenylacetamido)-spiro[penam-2,4'-piperidine]-3-carboxylic acid (a) Benzyl 1'-methyl-6-(2-phenylacetamido)-spiro[penam-2,4'-piperidine]-3-carboxylate Benzyl 6-amino-1'-methyl-spiro[penam-2,4'-piperidine]-3-carboxylate di-p-toluenesulfonate (8.5 g=0.012 mole) (prepared according to the method described in Example 1.8.1 of our Application Ser. No. 06/162,616, filed June 24, 1980 is converted into the free base by dissolving it in 200 ml of dichloromethane and adding 2.44 g (0.024 mole) of triethylamine. The solution is cooled to −10° C. and is treated simultaneously with a solution of 1.86 g (0.012 mole) of phenylacetyl chloride in 40 ml of dichloromethane and with a solution of 1.24 g (0.012 mole) of triethylamine in 40 ml of dichloromethane, the addition taking approximately 1 hour.

Stirring is continued for 2 hours, the temperature being allowed to return to 0° C., whereupon the solution is washed successively with water, with a saturated aqueous sodium hydrogen carbonate solution and again with water. After evaporation to dryness, 4.4 g of benzyl 1'-methyl-6-(2-phenylacetamido)-spiro[penam-2,4'-piperidine]-3-carboxylate are obtained. Yield: 76.2%; M.P. 124°-125° C.

Infra-red spectrum (KBr) in cm$^{-1}$: 3318 (NH); 1800 (beta-lactam); 1740 (ester); 1670 (amide); 690, 740 (monosubstituted phenyl).

NMR spectrum (CDCl$_3$-TMS): H$_3$: singlet at 4.52 ppm; H$_5$: doublet at 5.47 ppm; H$_6$: doublet at 5.65 ppm; H$_5$ and H$_6$ are coupled; J=4.1 Hz.

Mass spectrum: M$^+$·m/e=479.

(b)
1'-Methyl-6-(2-phenylacetamido)-spiro[penam-2,4'-piperidine]-3-carboxylic acid Under a hydrogen pressure of 3.2 kg/cm$^2$ and in the presence of 4.4 g of palladium on carbon (10% Pd), a solution of 4.4 g (0.091 mole) of benzyl 1'-methyl-6-(2-phenylacetamido)-spiro[penam-2,4'-piperidine]-3-carboxylate prepared in I.1.a) in 800 ml of ethanol are hydrogenolyzed in a Parr's apparatus for 1 hour. After filtering, the precipitate is digested in 1.5 liter of a 9:1 v/v methanol-water mixture for 1 hour. Evaporation of the filtrate to dryness gives 1.6 g of 1'-methyl-6-(2-phenylacetamido)-spiro[penam-2,4'-piperidine]-3-carboxylic acid. Yield: 44.8%; M.P. 189°-190° C. (decomposition).

Infra-red spectrum (KBr): 1770 cm$^{-1}$ (beta-lactam). Mass spectrum: M−44 (CO$_2$): m/e=345.

Analysis for C$_{19}$H$_{23}$N$_3$O$_4$S (M.W. 389.483): calculated (%): C 58.59; H 5.95; N 10.78; S 8.23; found (%): C 56.7 H, 6.1; N 10.20; S 7.20.

I.2. Preparation of 1'-benzyl-6-(2-phenylacetamido)-spiro[penam-2,4'-piperidine]-3-carboxylic acid (a) Benzyl 1'-benzyl-6-(2-phenylacetamido)-spiro[penam-2,4'-piperidine]-3-carboxylate Benzyl 6-amino-1'-benzyl-spiro[penam-2,4'-piperidine]-3-carboxylate di-p-toluenesulfonate (7.82 g=0.01 mole) (prepared according to the method described in Example I.8.2 of our Application Ser. No. 06/162,616, filed June 24, 1980) is converted into the free base by dissolving it in 120 ml of dichloromethane and adding 2.023 g (0.02 mole) of triethylamine. The solution is cooled to −10° C. and is treated slowly and simultaneously with a solution of 1.55 g (0.01 mole) of phenylacetyl chloride in 40 ml of dichloromethane and with a solution of 1.01 g (0.01 mole) of triethylamine in 40 ml of dichloromethane.

Stirring is continued for 2 hours, allowing the temperature to return to 0° C. The solution is washed successively with water, with a saturated aqueous solution of sodium hydrogen carbonate and again with water. After evaporation to dryness and crystallization of the residue from cyclohexane, benzyl 1'-benzyl-6-(2-phenylacetamido)-spiro[penam-2,4'-piperidine]-3-carboxylate is obtained, which is subjected as such to step I.2.b; yield: 71%; M.P. 130°-131° C.

Infra-red spectrum (KBr) in cm$^{-1}$: 1792 (beta-lactam); 1750 (ester); 701-740 (monosubstituted phenyl).

Mass spectrum: M$^+$·m/e=555, M−33 (SH): m/e=522; M−91 (C$_7$H$_7$): m/e=464.

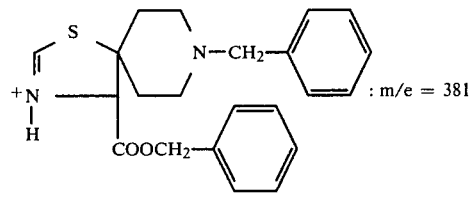
: m/e = 381

Analysis for C$_{32}$H$_{33}$N$_3$O$_4$S (M.W. 555.706): calculated (%): C 69.16; H 5.99; N 7.56; found (%): C 71.72; H 5.87; N 8.01.

(b)
1'-Benzyl-6-(2-phenylacetamido)-spiro[penam-2,4'-piperidine]-3-carboxylic acid Under a hydrogen pressure of 3.2 kg/cm$^2$ and in the presence of 4 g of palladium on carbon (10% Pd), a solution of benzyl 1'-benzyl-6-(2-phenylacetamido)-spiro[penam-2,4'-piperidine]-3-carboxylate (prepared in I.2.a) in 800 ml of ethanol is hydrogenolyzed in a Parr's apparatus for 1,5 hours, then filtered and the filtrate is evaporated to dryness in a vacuum and the residue is triturated in isopropyl alcohol. 1'-Benzyl-6-(2-phenylacetamido)-spiro[penam-2,4'-piperidine]-3-carboxylic acid is thus obtained in a yield of 71%; M.P. 170°-171° C. (decomposition).

NMR spectrum (DMSO-TMS): H$_3$: singlet at 4.2 ppm;

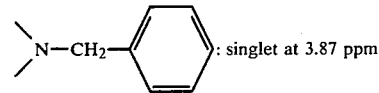
: singlet at 3.87 ppm

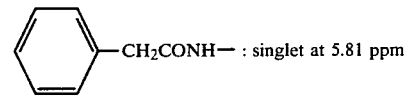
—CH$_2$CONH— : singlet at 5.81 ppm

Mass spectrum: no M$^+$·M−18 (H$_2$O): m/e=447; M−44 (CO$_2$): m/e=421.

Analysis for C$_{25}$H$_{27}$N$_3$O$_4$S (M.W. 465.581): calculated (%): C 64.49; H 5.84; N 9.02; found (%): C 62.19; H 6.03; N 8.57.

I.3. Preparation of 1'-phenyl-6-(2-phenylacetamido)-spiro[penam-2,4'-piperidine]-3-carboxylic acid (a) Benzyl 1'-phenyl-6-(2-phenylacetamido)-spiro[penam-2,4'-piperidine]-3-carboxylate To a suspension of 1.53 g (0.002 mole) of benzyl 6-amino-1'-phenyl-spiro[penam-2,4'-piperidine]-3-carboxylate di-p-toluenesulfonate (prepared according to the method described in Example I.8.3. of our Application Ser. No. 06/162,616, filed June 24, 1980) in 100 ml of anhydrous dichloromethane is added all at once 404 mg (0.004 mole) of triethylamine in 10 ml of dichloromethane. The solution is cooled to a temperature of from 0° to −5° C. and then there are simultaneously added dropwise a solution of 340 mg (0.022 mole) of phenylacetyl chloride in 30 ml of dichloroemethane and a solution of 220 mg (0.022 mole) of triethylamine in 30 ml of dichloromethane, the addition taking place over the course of about 1 hour. Thereafter, the reaction mixture is stirred for 3 hours at 15° C., then successively washed with water, with a saturated aqueous solution of sodium hydrogen carbonate and again with water. After evaporating the solution to dryness and recrystallizing the residue from ethyl acetate/hexane (1:3 v/v), there are obtained 950 mg of benzyl 1'-phenyl-6-(2-phenylacetamido)-spiro[penam-2,4'-piperidine]-3-carboxylate. Yield: 88%; M.P. 120°–121° C.

IR spectrum (KBr) in cm$^{-1}$: 3300 (NH); 1754, 1728, 1635 (CO).

NMR spectrum (CDCl$_3$-TMS): 3 phenyls: multiplet at 7.55 to 6.65 ppm; H$_6$: doublet at 5.78 ppm; H$_5$: doublet at 5.45 ppm;

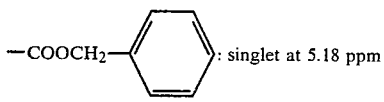

H$_3$: singlet at 4.57 ppm;

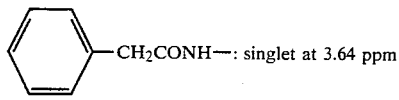

Analysis for C$_{31}$H$_{31}$N$_3$O$_4$S (M.W. 541.65): calculated (%): C 68.74; H 5.77; N 7.76; found (%): C 68.80; H 5.59; N 7.50.

(b)
1'-Phenyl-6-(2-phenylacetamido)-spiro[penam-2,4'-piperidine]-3-carboxylic acid A solution of 470 mg (0.000869 mole) of benzyl 1'-phenyl-6-(2-phenylacetamido)-spiro[penam-2,4'-piperidine]-3-carboxylate (as prepared in I.3.a) in 200 ml of anhydrous ethanol is hydrogenolyzed in a Parr's apparatus for 2 hours in the presence of 500 mg of palladium on carbon (10% Pd) at ambient temperature and at a hydrogen pressure of 3.5 kg/cm$^2$. The reaction mixture is then filtered, the filtrate is evaporated to dryness and the residue is taken up in diethyl ether. The precipitate is filtered and washed with diethyl ether. There are thus obtained 310 mg of 1'-phenyl-6-(2-phenylacetamido)-spiro[penam-2,4'-piperidine]-3-carboxylic acid. Yield: 96%; M.P. 153°–154° C. (decomposition).

IR spectrum (KBr) in cm$^{-1}$: 1770 (beta-lactam CO); 1645 (amide CO).

NMR spectrum (DMSO-TMS): NH: multiplet at 8.95 to 8.70 ppm; 2 phenyls: multiplet at 7.5 to 6.6 ppm; H$_5$ and H$_6$: multiplet at 5.6 to 5.3 ppm; H$_3$: singlet at 4.46 ppm.

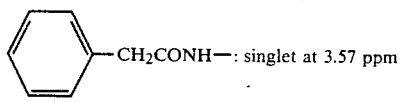

Analysis for C$_{24}$H$_{25}$N$_3$O$_4$S (M.W. 451.53): calculated (%): C 63.84; H 5.58; N 9.31; found (%): C 61.60; H 5.36; N 8.52.

EXAMPLE II

Preparation of 6-(2,6-dimethoxybenzamido)-spiro[penam-2,4'-piperidine]-3-carboxylic acids II.1. Preparation of 6-(2,6-dimethoxybenzamido)-1'-methyl-spiro[penam-2,4'-piperidine]-3-carboxylic acid (a) Benzyl 6-(2,6-dimethoxybenzamido)-1'-methyl-spiro[penam-2,4'-piperidine]-3-carboxylate Benzyl 6-amino-1'-methyl-spiro[penam-2,4'-piperidine]-3-carboxylate di-p-toluenesulfonate (4.94 g=0.007 mole) (prepared as indicated in Example I.1.a) is converted into the free base by dissolving it in 80 ml of dichloromethane and adding 1.42 g (0.014 mole) of triethylamine, followed by cooling to −10° C. It is then treated dropwise and simultaneously with a solution of 1.40 g (0.007 mole) of 2,6-dimethoxybenzoyl chloride in 20 ml of dichloromethane and with a solution of 0.71 g (0.007 mole) of triethylamine in 20 ml of dichloromethane, the period of addition being approximately 1 hour.

Stirring is continued for 2 hours, the temperature being allowed to return to 0° C. The solution is then washed successively with water, with an aqueous solution of sodium hydrogen carbonate and again with water. After evaporation to dryness and crystallization of the residue from ethyl acetate, 2.5 g of benzyl 6-(2,6-dimethoxybenzamido)-1'-methyl-spiro[penam-2,4'-piperidine]-3-carboxylate are obtained; yield: 68%; M.P. 97° C. (decomposition).

Infra-red spectrum (KBr): 1792 cm$^{-1}$ (beta-lactam).

NMR spectrum (CDCl$_3$-TMS): H$_3$: singlet at 4.61 ppm; H$_5$: doublet at 5.25 ppm; H$_6$: doublets at 5.96 ppm; NH: doublet at 6.60 ppm; H$_5$ and H$_6$ are coupled, J=4.1 Hz; H amino and H$_6$ are coupled, J=8 Hz.

Mass spectrum: M$^+$·m/e=525.

Analysis for C$_{27}$H$_{31}$N$_3$O$_6$S (M.W. 525.635): calculated (%): C 61.70; H 5.94; N 7.99; found (%): C 60.85; H 6.29; N 7.38.

(b)
6-(2,6-Dimethoxybenzamido)-1'-methyl-spiro[penam-2,4'-piperidine]-3-carboxylic acid Under a hydrogen pressure of 3.2 kg/cm$^2$ and in the presence of 1.5 g of palladium on carbon (10% Pd), a solution of 2 g (0.0038 mole) of benzyl 6-(2,6-dimethoxybenzamido)-1'-methyl-spiro[penam-2,4'-piperidine]-3-carboxylate (prepared in II.1.a) in 700 ml of ethanol is hydrogenolyzed in a Parr's apparatus for 1 hour. This is followed by filtration, the filtrate being evaporated to dryness and the residue washed with a little ethanol. 1.2 g of 6-(2,6-dimethoxybenzamido)-1'-methyl-spiro[penam-2,4'-piperidine]-3-carboxylic acid is thus obtained; yield: 60.4%; M.P. 193°–194° C. (decomposition).

Infra-red spectrum (KBr): 1779 cm$^{-1}$ (beta-lactam).

NMR spectrum (DMSO-TMS): H$_3$: singlet at 3.96 ppm; NH: doublet at 8.92 ppm; H amino and H$_6$ are coupled, J=7.3 Hz.

Analysis for C$_{20}$H$_{25}$N$_3$O$_6$S (M.W. 435.510): calculated (%): C 55.16; H 5.18; N 9.64; found (%): C 51.06; H 6.51; N 8.92.

II.2. Preparation of 1′-benzyl-6-(2,6-dimethoxybenzamido)-spiro[penam-2,4′-piperidine]-3-carboxylic acid The following compounds are prepared in the same way as in II.1:

(a) benzyl 1′-benzyl-6-(2,6-dimethoxybenzamido)-spiro[penam-2,4′-piperidine]-3-carboxylate;

(b) 1′-benzyl-6-(2,6-dimethoxybenzamido)-spiro[penam-2,4′-piperidine]-3-carboxylic acid.

EXAMPLE III

Preparation of 6-[D(−)-(2-amino-2-phenylacetamido)-]-spiro[penam-2,4′-piperidine]-3-carboxylic acids

III.1. Preparation of 6-[D(−)-(2-amino-2-phenylacetamido)]-1′-methyl-spiro]penam-2,4′-piperidine]-3-carboxylic acid (a) Benzyl 6-[D(−)-(2-benzyloxycarbonylamino-2-phenylacetamido)]-1′-methyl-spiro[penam-2,4′-piperidine]-3-carboxylate Benzyl 6-amino-1′-methyl-spiro[penam-2,4′-piperidine]-3-carboxylate di-p-toluenesulfonate (9 g=0.0127 mole) (prepared as indicated in Example I.1.a) is converted into the free base by dissolving it in 120 ml of dichloromethane and adding 2.57 g (0.025 mole) of triethylamine. To the resulting solution are added 3.71 g (0.013 mole) of N-(benzyloxycarbonyl)-D(−)-2-phenylglycine and 4 g of diisopropylcarbodiimide. After 24 hours, there is filtered and excess solvent and reagent are evaporated from the filtrate in a vacuum. The evaporation residue is passed through a silica gel (60 Merck) column, eluating first with chloroform and then with acetone. The resulting acetone solution is then evaporated to dryness, the residue is taken up with chloroform and the resulting solution is filtered and again evaporated to dryness. After crystallization of the residue from acetonitrile, 0.9 g of benzyl 6-[D(−)-(2-benzyloxycarbonylamino-2-phenylacetamido)]-1′-methyl-spiro[penam-2,4′-piperidine]-3-carboxylate is obtained, contamined by a little 1,3-diisopropylurea; M.P. 141°–141.5° C.

Infra-red spectrum (KBr) in cm$^{-1}$: 3325 (NH); 1790 (beta-lactam); 695, 745 (monosubstituted phenyl).

NMR spectrum (CDCl$_3$-TMS):

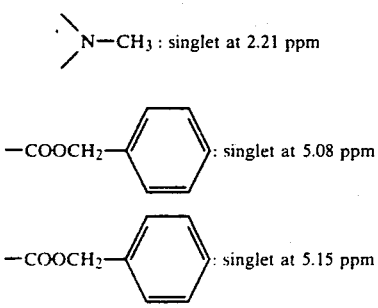

H$_3$: singlet at 4.54 ppm; H$_5$: doublet at 5.2 ppm; H$_6$: doublet at 5.7 ppm.

(b) 6-[D(−)-(2-Amino-2-phenylacetamido)]-1′-methyl-spiro[penam-2,4′-piperidine]-3-carboxylic acid Under a hydrogen pressure of 3.2 kg/cm$^2$ and in the presence of 1.2 g of palladium on carbon (10% Pd), a solution of 1.15 g (0.0018 mole) of benzyl 6-[D(−)-(2-benzyloxycarbonylamino-2-phenylacetamido)]-1′-methyl-spiro[penam-2,4′-piperidine]-3-carboxylate (prepared in III.1.a) in 600 ml of ethanol is hydrogenolyzed in a Parr's apparatus for 3 hours. After evaporation to dryness and crystallization of the residue from isopropyl alcohol, 0.5 g of 6-[D(−)-(2-amino-2-phenylacetamido)]-1′-methyl-spiro[penam-2,4′-piperidine]-3-carboxylic acid is obtained; yield: 67.9%; M.P. 185° C. (decomposition).

Infra-red spectrum (KBr) in cm$^{-1}$: 3412 (NH$_2$); 1780 (beta-lactam); 1680 (amide); 1615 (COO$^-$).

NMR spectrum (DMSO-TMS): 2H$_{2′}$, 2H$_{3′}$, 2H$_{5′}$ and 2H$_{6′}$: multiplet at 1.5 to 3.8 ppm; H$_3$: singlet at 3.96 ppm; H$_5$+H$_6$: multiplet at 5.1 to 5.7 ppm; 5H of the phenyl: multiplet at 7.35 ppm; NH: broad at 9.05 ppm.

III.2. Preparation of 6-[D(−)-(2-amino-2-phenylacetamido)]-1′-benzyl-spiro[penam-2,4′-piperidine]-3-carboxylic acid (a) Benzyl 1′-benzyl-6-[D(−)-(2-benzyloxycarbonylamino-2-phenylacetamido)]-spiro[penam-2,4′-piperidine]-3-carboxylate Benzyl 6-amino-1′-benzyl-spiro[penam-2,4′-piperidine]-3-carboxylate di-p-toluenesulfonate (9.93 g=0.0127 mole) (prepared as indicated in Example I.2.a) is converted into the free base by dissolving it in 200 ml of dichloromethane and adding 2.57 g (0.0254 mole) of triethylamine. To the resulting solution are added 3.70 g (0.013 mole) of N-(benzyloxycarbonyl)-D(−)-2-phenylglycine and 7 g of diisopropylcarbodiimide. After 24 hours, there is filtered and the filtrate is evaporated in a vacuum. The residue is passed through a column of silica gel (60 Merck), using chloroform as eluant. After two passes, the eluate is evaporated to dryness and gives 1.2 g of benzyl 1′-benzyl-6-[D(−)-(2-benzyloxycarbonylamino-2-phenylacetamido)]-spiro[penam-2,4′-piperidine]-3-carboxylate; M.P. 72°–73° C.

Infra-red spectrum (KBr) in cm$^{-1}$: 1793 (beta-lactam); 1737, 1749 (ester); 1685 (amide); 698, 742 (monosubstituted phenyl).

NMR spectrum (CDCl$_3$-TMS):

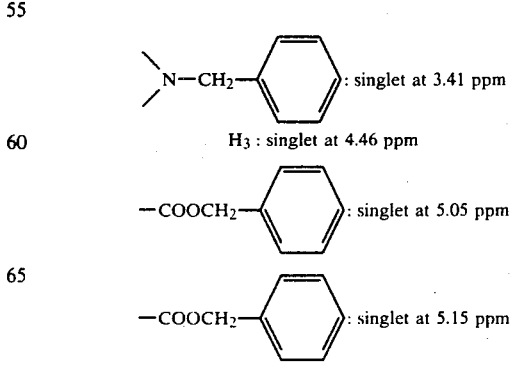

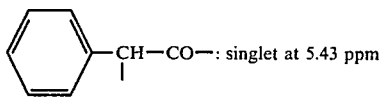: singlet at 5.43 ppm

Mass spectrum: M+·m/e=704

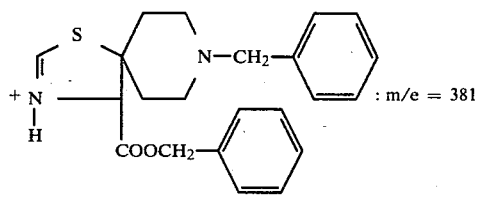: m/e = 381

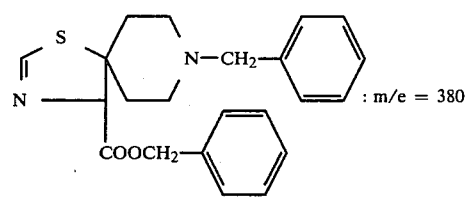: m/e = 380 ditto −33 (Sh): m/e=347.

Analysis for $C_{40}H_{40}N_4O_6S$ (M.W. 704.858); calculated (%): C 68.27; H 5.72; N 7.94; found (%): C 68.17; H 5.60; N 8.26.

(b)
6-[D(−)-(2-Amino-2-phenylacetamido)]-1'-benzyl-spiro[penam-2,4'-piperidine]-3-carboxylic acid Under a hydrogen pressure of 3 kg/cm² and in the presence of 1 g of palladium on carbon (10% Pd), a solution of 1.2 g (0.0017 mole) of benzyl 1'-benzyl-6-[D(−)-(2-benzyloxycarbonylamino-2-phenylacetamido)]-spiro[penam-2,4'-piperidine]-3-carboxylate (prepared in III.2.a) in 250 ml of ethanol is hydrogenolyzed in a Parr's apparatus for about 3 hours. After filtering, the filtrate is evaporated to dryness and 0.3 g of 6-[D(−)-(2-amino-2-phenyl-acetamido)]-1'-benzyl-spiro[penam-2,4'-piperidine]-3-carboxylic acid is obtained; M.P. >195° C. (decomposition).

Infra-red spectrum (KBr) in cm⁻¹: 3415 (NH₂); 1785 (beta-lactam); 1680 (amide); 1615 (COO⁻); 700, 750 (monosubstituted phenyl).

Mass spectrum of the methyl ester (obtained by esterification with diazomethane): M+·: m/e=494; [M+H]+·: m/e=495; [M−H]+·: m/e=493; M−33(SH): m/e=461; M−59 (COOCH₃): m/e=435.

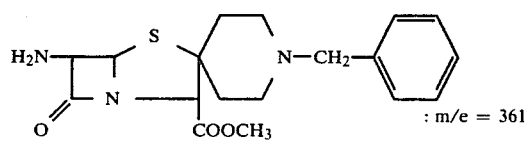: m/e = 361

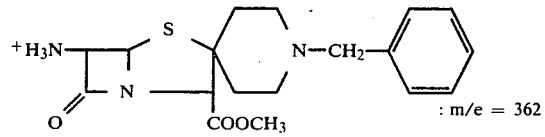: m/e = 362

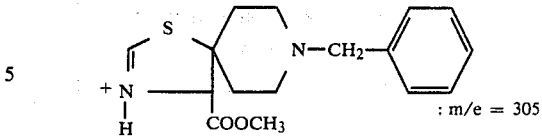: m/e = 305

Analysis for $C_{25}H_{28}N_4O_4S$ (M.W. 480.587): calculated (%): C 62.47; H 5.87; N 11.66; found (%): C 56.76; H 5.90; N 9.40.

III.3. Preparation of 6-[D(−)-(2-amino-2-phenylacetamido)]-1'-phenyl-spiro[penam-2,4'-piperidine]-3-carboxylic acid (a) Benzyl 6-[D(−)-(2-benzyloxycarbonylamino-2-phenylacetamido)]-1'-phenyl-spiro[penam-2,4'-piperidine]-3-carboxylate To a suspension of 1.53 g (0.002 mole) of benzyl 6-amino-1'-phenyl-spiro[penam-2,4'-piperidine]-3-carboxylate di-p-toluenesulfonate (prepared as indicated in Example I.3.a) in 50 ml of dichloromethane is added, at ambient temperature, 0.404 g (0.004 mole) of triethylamine in 5 ml of dichloromethane. The solution is then cooled to a temperature of from 0° to −5° C. and then there are successively added 0.630 g (0.002 mole) of N-(benzyloxycarbonyl)-D(−)-2-phenylglycine in 10 ml of dichloromethane, followed by a solution of 0.460 g dicyclohexylcarbodiimide in 30 ml of dichloromethane. The reaction mixture is stirred for 1 hour at about 5° C. and then overnight at ambient temperature. The precipitate obtained is filtered off and the filtrate is successively washed with water, a saturated aqueous solution of sodium hydrogen carbonate and again with water and then dried and evaporated to dryness. The residue is recrystallized from an ethyl acetate-hexane mixture (1:3 v/v) to give 1.36 g of benzyl 6-[D(−)-(2-benzyloxycarbonylamino-2-phenylacetamido)]-1'-phenyl-spiro[penam-2,4'-piperidine)-3-carboxylate. Yield: 99%; M.P. 167°-168° C.

IR spectrum (KBr) in cm⁻¹: 3320 (NH); 1765, 1730, 1664 (CO).

NMR spectrum (CDCl₃-TMS): 4 phenyls: multiplet at 7.55 to 6.55 ppm; H₅, H₆ and 2

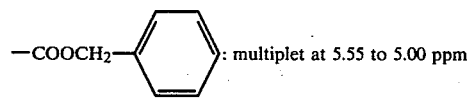: multiplet at 5.55 to 5.00 ppm

H₃: singlet at 4.56 ppm.

Analysis for $C_{39}H_{38}N_4O_6S$ (M.W. 690.79): calculated (%): C 67.80; H 5.54; N 8.11; found (%): C 67.36; H 5.93; N 8.23.

(b)
6-[D(−)-(2-amino-2-phenylacetamido)]-1'-phenyl-spiro[penam-2,4'-piperidine]-3-carboxylic acid A solution of 690 mg of benzyl 6-[D(−)-(2-benzyloxycarbonylamino-2-phenylacetamido)]-1'-phenyl-spiro[penam-2,4'-piperidine]-3-carboxylate (prepared in III.3.a) in 200 ml of absolute ethanol is hydrogenolyzed at ambient temperature for 4 hours in a Parr's apparatus under a hydrogen pressure of 3.5 kg/cm² in the presence of 1 g of palladium on carbon (10% Pd). The reaction mixture is then filtered and the filtrate is washed with ethanol and evaporated to dryness. The residue is taken up in diethyl ether and filtered to give 120 mg of 6-[D(−)-(2-amino-2-phenylacetamido)]-1′-phenyl-spiro[penam-2,4′-piperidine]-3-carboxylic acid. Yield: 26%; M.P. 187°–189° C. (decomposition).

IR spectrum (KBr) in cm$^{-1}$: 1765 (beta-lactam CO), 1675 (amide).

Analysis for $C_{24}H_{26}N_4O_4S$ (M.W. 466.55): calculated (%): C 61.78; H 5.62; N 12.01; found (%): C 57.90; H 5.81; N 10.07.

Pharmacological properties.

Various comparative tests have been carried out to ascertain the intrinsic biological activity of compounds of general formula (I) against various bacterial strains of the Gram-positive and Gram-negative type. The reference compounds were penicillin G, ampicillin and methicillin. Information will first be given about the origin and characteristics of the bacterial strains used.

A. Gram-positive bacterial strains.

*Staphylococcus aureus* 6538.

This is a Gram-positive coccus which is particularly sensitive to penicillins and which has a low mechanism of resistance. This strain of Staphylococcus is, therefore, representative of a maximum sensitivity of the species.

*Staphylococcus aureus* 52149.

This is a Gram-positive coccus, the intrinsic sensitivity of the receptor of which is equivalent to the preceding strain but which produces a beta-lactamase typical of the type, which renders it resistant to all penicillins sensitive to hydrolysis.

B. Gram-negative bacterial strains.

*Escherichia coli* B.

This is a well-known collection strain of *Escherichia coli* which produces very little beta-lactamase (of type I) and it is, therefore, very sensitive to penicillin. With regard to the classification of the beta-lactamases, use is here made of that proposed by M. H. Richmond and R. B. Sykes in Advances in Microbial Physiology, 9, (1973), 43 and 45.

*Escherichia coli* B-AMPI R.

This is a mutant of the preceding strain, which we have produced. This strain is, on the contrary, a hyper-producer of beta-lactamase of type I, already produced by the parent strain *E. coli* B. It has an increased resistance to the penicillins, which would appear to be directly connected to the production of beta-lactamase.

*Escherichia coli* K 12.

This is a well-known collection strain which produces very little beta-lactamase of type I and which is, therefore, very sensitive to pencillins.

*Escherichia coli* K 12-44-S.

This is a pleitropic mutant of *E. coli* K 12-44 (which is, in turn, a mutant of *E. coli* K 12). This mutant is not a producer of beta-lactamase and is very sensitive to penicillins due to hyper-permeability.

*Escherichia coli* K 12-44-S-TEM.

This strain is obtained from a strain of *E. coli* K 12-44-S to which the TEM episome, which is responsible particularly for the production of a beta-lactamase of type III, has been transferred.

*Escherichia coli* K 12-44-S-RP$_1$*

This strain is obtained from a strain of *E. coli* K 12-44-S to which has been transferred the RP$_1$* episome, which is responsible for a resistance factor to penicillins due to impermeability of the bacterial cell wall.

C. Results of the comparative activity tests.

According to a procedure described hereinafter, the minimum inhibitory concentration (abbreviated to MIC) of the growth of bacteria was determined for a number of compounds of general formula (I).

The products to be tested are introduced, in increasing concentrations, into a gelose culture medium in Petri dishes. A multiple inoculator is used to deposit simultaneously onto the surface of the medium drops (in all 10 microliters) of inoculum (suspension of about $10^5$ bacteria per ml). After incubation at 37° C. for 24 hours, the growth of the bacteria is observed. By definition, the MIC is expressed by the minimum concentration (expressed in terms of micromoles per milliter) inhibiting multiplication of the bacteria. However, in the results which follow, the MIC is considered to be equal to 1 for the reference compounds and the figures indicating the activity of the compounds of general formula (I) tested are, therefore, relative values. This presentation of the results is more correct and the most reproducible because, for one and the same bacterial strain, different MIC values can be observed if they are measured at different times. This is bound up with the "seasonal" variations in the strains and their nutrient medium.

The compounds tested are the following:

Compound A: 1′-methyl-6-(2-phenylacetamido)-spiro[penam-2,4′-piperidine]-3-carboxylic acid.
Compound B: 1′-benzyl-6-(2-phenylacetamido)-spiro[penam-2,4′-piperidine]-3-carboxylic acid.
Compound C: 1′-phenyl-6-(2-phenylacetamido)-spiro[penam-2,4′-piperidine]-3-carboxylic acid.
Compound D: 6-(2,6-dimethoxybenzamido)-1′-methyl-spiro[penam-2,4′-piperidine]-3-carboxylic acid.
Compound E: 6-[D(−)-(2-amino-2-phenylacetamido)]-1′-methyl-spiro[penam-2,4′-piperidine]-3-carboxylic acid.
Compound F: 6-[D(−)-(2-amino-2-phenylacetamido)]-1′-benzyl-spiro[penam-2,4′-piperidine]-3-carboxylic acid.
Compound G: 6-[D(−)-(2-amino-2-phenylacetamido)]-1′-phenyl-spiro[penam-2,4′-piperidine]-3-carboxylic acid.

| (a) Comparative tests with penicillin G. | | | | |
|---|---|---|---|---|
| Bacterial strain | Penicillin G | Compound A | Compound B | Compound C |
| S.AUREUS 6538 | 1 | 0.5 | 0.3 | 0.2 |
| S.AUREUS 52149 | 1 | 2 | 0.5 | 0.5 |
| E.COLI B-AMPI R | 1 | 1 | 2 | 0.3 |
| E.COLI K 12-44-S-TEM | 1 | 2 | 2 | 0.3 |
| E.COLI K 12-44-S-RP$_1$* | 1 | 1 | 1 | 0.5 |

| (b) Comparative tests with methicillin. | | |
|---|---|---|
| Bacterial strain | Methicillin | Compound D |
| S.AUREUS 6538 | 1 | 0.1 |
| S.AUREUS 52149 | 1 | 0.1 |
| E.COLI K 12-44-S-TEM | 1 | 0.5 |

-continued (c) Comparative tests with ampicillin.

| Bacterial strain | Ampicillin | Compound E | Compound F | Compound G |
| --- | --- | --- | --- | --- |
| S.AUREUS 6538 1 | 2 | 1 | 1 | |
| S.AUREUS 52149 | 1 | 0.5 | 1 | 2 |
| E.COLI B-AMPI R | 1 | 2 | — | 0.3 |
| E.COLI K 12-44-S-TEM | 1 | 0.5 | 0.5 | 0.12 |
| E.COLI K 12-44-S-RP₁* | 1 | 0.125 | 0.25 | 0.25 |

It follows from these results that the compounds of general formula (I) according to the present invention exhibit levels of activity which are higher than those of the corresponding traditional penicillins against both Gram-positive and Gram-negative bacteria. Furthermore, this superiority of action is very marked against bacterial strains which are resistant to penicillins (S. aureus 52149, E. coli B-Ampi R, E. coli K 12-44-S-TEM and E. coli K 12-44-S-RP₁*).

D. Activity "in vivo".

This is shown by a classical septicemia test induced in mouse by Diplococcus pneumoniae.

Experimental infection is produced in mice by intraperitoneal injection of a diluted culture of a Diplococcus pneumoniae (strain 53 145 obtained from Institut Pasteur-Paris). The number of bacteria injected corresponds to about 100 times LD$_{50}$.

The drug to be tested, dissolved in a physiological salt solution, is administered subcutaneously to the mice, once at the time of infection and a second time 5 hours later.

The following Table gives the results obtained with both compound A according to the invention and the corresponding penicillin G. The dose is expressed in micromole/kg of animal body weight. The ratios given for each of the compounds tested at a given dose indicate the number of mice that have survived 10 days after infection out of the total number of mice tested:

TABLE

| Dose | Penicillin G | Compound A |
| --- | --- | --- |
| 0.50 | 0/10 | 8/10 |
| 1.00 | 0/10 | 9/10 |
| 2.00 | 9/10 | 10/10 |

From this Table, it can be seen that at a dose of 0.50 micromole/kg of compound A, 8 mice out of 10 have survived, while none of the mice administered with penicillin G at that dose have survived. A similar number of surviving mice when administered with penicillin G is only obtained at a dose of 2,00 micromoles/kg, i.e. four times higher. In this test, compound A is therefore about four times more active than penicillin G.

E. Posology and use.

The compounds of formula (I), just like the penicillins, can be administered orally or parenterally.

Generally speaking, the dosage is from 0.2 g to 8 g of compound per day, these doses being, of course, liable to adaptation in function of the patient, the disease to be treated and the method of administration.

Thus, the present invention also provides pharmaceutical compositions for oral or parenteral administration comprising at least one of the new compounds, in admixture with the usual solid or liquid pharmaceutical diluents or carriers.

We claim:

1. A 6-amino-spiro[penam-2,4'-piperidine]-3-carboxylic acid having the formula

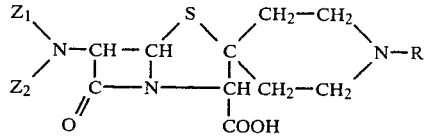

wherein R is a methyl, phenyl or benzyl, $Z_1$ is a hydrogen atom and $Z_2$ is a radical selected from the group consisting of phenylacetyl, 2-amino-2-phenylacetyl, 5-methyl-3-phenyl-4-isoxazolecarbonyl and 2,6-dimethoxybenzoyl, or $Z_1$ and $Z_2$ together represent (hexahydro-1H-azepin-1-yl)methylene, or a therapeutically acceptable non-toxic salt thereof.

2. A compound as claimed in claim 1, namely 1'-methyl-6-(2-phenyl-acetamido)-spiro[penam-2,4'-piperidine]-3-carboxylic acid.

3. A compound as claimed in claim 1, namely 1'-benzyl-6-(2-phenylacetamido)-spiro[penam-2,4'-piperidine]-3-carboxylic acid.

4. A compound as claimed in claim 1, namely 1'-phenyl-6-(2-phenylacetamido)-spiro[penam-2,4'-piperidine]-3-carboxylic acid.

5. A compound as claimed in claim 1, namely 6-(2,6-dimethoxybenzamido)-1'-methyl-spiro[penam-2,4'-piperidine]-3-carboxylic acid.

6. A compound as claimed in claim 1, namely 6-[D(−)-(2-amino-2-phenylacetamido)]-1'-methyl-spiro[penam-2,4'-piperidine]-3-carboxylic acid.

7. A compound as claimed in claim 1, namely 6-[D(−)-(2-amino-2-phenylacetamido)]-1'-benzyl-spiro[penam-2,4'-piperidine]-3-carboxylic acid.

8. A compound as claimed in claim 1, namely 6-[D(−)-(2-amino-2-phenylacetamido)]-1'-phenyl-spiro[penam-2,4'-piperidine]-3-carboxylic acid.

9. An antibacterial composition which comprises a pharmaceutical carrier and an antibacterially effective amount of a 6-amino-spiro[penam-2,4'-piperidine]-3-carboxylic acid of the formula

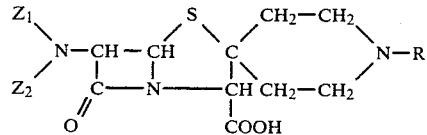

wherein R is a methyl, phenyl or benzyl, $Z_1$ is a hydrogen atom and $Z_2$ is a radical selected from the group consisting of phenylacetyl, 2-amino-2-phenylacetyl, 5-methyl-3-phenyl-4-isoxazolecarbonyl and 2,6-dimethoxybenzoyl, or $Z_1$ and $Z_2$ together represent (hexahydro-1H-azepin-1-yl)methylene, or a therapeutically acceptable non-toxic salt thereof.

10. A method of treating infectious diseases caused by Gram-positive and Gram-negative bacteria in warm-blooded animals, which comprises administering to said animals an antibacterially effective amount of a 6- amino-spiro[penam-2,4'-piperidine]-3-carboxylic acid of the formula

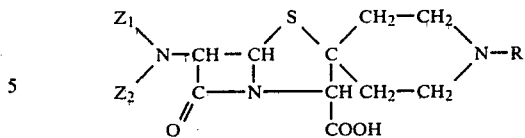

wherein R is a methyl, phenyl or benzyl, $Z_1$ is a hydrogen atom and $Z_2$ is a radical selected from the group consisting of phenylacetyl, 2-amino-2-phenylacetyl, 5-methyl-3-phenyl-4-isoxazolecarbonyl and 2,6-dimethoxybenzoyl, of $Z_1$ and $Z_2$ together represent (hexahydro-1H-azepin-1-yl)methylene, or a therapeutically acceptable non-toxic salt thereof.

* * * * *